United States Patent
Yagyu

(10) Patent No.: US 10,654,882 B2
(45) Date of Patent: May 19, 2020

(54) NICOTINAMIDE MONONUCLEOTIDE DERIVATIVE AND SALT THEREOF, METHOD FOR PRODUCING SAME, TOPICAL SKIN PREPARATION, COSMETIC AND FOOD ADDITIVE

(71) Applicant: SHOWA DENKO K.K., Tokyo (JP)

(72) Inventor: Daisuke Yagyu, Ichihara (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 15/777,756

(22) PCT Filed: Nov. 16, 2016

(86) PCT No.: PCT/JP2016/083942
§ 371 (c)(1),
(2) Date: May 21, 2018

(87) PCT Pub. No.: WO2017/110317
PCT Pub. Date: Jun. 29, 2017

(65) Prior Publication Data
US 2018/0334474 A1 Nov. 22, 2018

(30) Foreign Application Priority Data

Dec. 21, 2015 (JP) ................................. 2015-249020

(51) Int. Cl.
| | | |
|---|---|---|
| *C07H 19/048* | (2006.01) | |
| *A61K 31/706* | (2006.01) | |
| *A23L 29/00* | (2016.01) | |
| *A61Q 19/08* | (2006.01) | |
| *A61K 8/60* | (2006.01) | |
| *A23L 33/13* | (2016.01) | |
| *A61Q 19/00* | (2006.01) | |

(52) U.S. Cl.
CPC ............ *C07H 19/048* (2013.01); *A23L 29/00* (2016.08); *A23L 33/13* (2016.08); *A61K 8/60* (2013.01); *A61K 8/606* (2013.01); *A61K 31/706* (2013.01); *A61Q 19/00* (2013.01); *A61Q 19/08* (2013.01); *A23V 2002/00* (2013.01)

(58) Field of Classification Search
CPC ......... A23L 33/13; A23L 29/00; A61K 8/606; A61K 8/60; A61K 31/706; A61K 19/08; A61Q 19/00; C07H 19/048; A23V 2002/00
See application file for complete search history.

(56) References Cited

U.S. PATENT DOCUMENTS

| | | | | |
|---|---|---|---|---|
| 7,846,970 B2 * | 12/2010 | Kamachi | ............ | A61K 8/0212 514/574 |
| 2007/0293577 A1 | 12/2007 | Kamachi et al. | | |
| 2017/0266213 A1 * | 9/2017 | Fu | ........ | A61K 31/706 |

FOREIGN PATENT DOCUMENTS

| | | |
|---|---|---|
| CN | 104771330 A | 7/2015 |
| CN | 104814974 A | 8/2015 |
| EP | 0 188 647 A1 | 7/1986 |
| JP | 61-176598 A | 8/1986 |
| JP | 2007-031415 A | 2/2007 |
| JP | 2007-522148 A | 8/2007 |
| JP | 2007-254393 A | 10/2007 |
| WO | 2004/013083 A1 | 2/2004 |
| WO | 2005/077886 A1 | 8/2005 |
| WO | 2015/186114 A1 | 12/2015 |
| WO | 2016/117465 A1 | 7/2016 |

OTHER PUBLICATIONS

Jun Yoshino, et al., "Nicotinamide Mononucleotide, a Key NAD Intermediate, Treats the Pathophysiology of Diet- and Age-Induced Diabetes in Mice", Cell Metabolism, Short Article, 2011, pp. 528-536, vol. 14.
Wujun Liu, et al., "Synthesis of phosphodiester-type nicotinamide adenine dinucleotide analogs", Tetrahedron, 2009, pp. 8378-8383, vol. 65.
Antonio Procopio, et al., "Lipophilic Hydroxytyrosol Esters: Fatty Acid Conjugates for Potential Topical Administration", Journal of Natural Products, 2011, pp. 2377-2381, vol. 74, No. 11, ISSN:0163-3864.
Shin-Ichiro Imai, "A possibility of nutriceuticals as an anti-aging intervention: Activation of sirtuins by promoting mammalian NAD biosynthesis", Pharmacological Research, 2010, pp. 42-47, vol. 62, No. 1, ISSN:1043-6618.
International Search Report for PCT/JP2016/083942 dated Jan. 31, 2017 [PCT/ISA/210].

* cited by examiner

*Primary Examiner* — Lawrence E Crane
(74) *Attorney, Agent, or Firm* — Sughrue Mion, PLLC

(57) ABSTRACT

The present invention provides a nicotinamide mononucleotide derivative, or salt thereof, which is a compound represented by general formula (1), wherein $R^1$ and $R^2$ respectively and independently represent a hydrogen atom or acyl group having 3 to 30 carbon atoms, the hydrocarbon group bound to the carbonyl carbon of the acyl group is a linear or branched, saturated or unsaturated hydrocarbon group, and at least one of $R^1$ and $R^2$ is the acyl group.

[Chemical Formula 1]

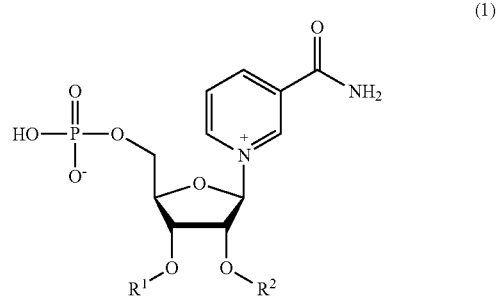

(1)

9 Claims, No Drawings

NICOTINAMIDE MONONUCLEOTIDE DERIVATIVE AND SALT THEREOF, METHOD FOR PRODUCING SAME, TOPICAL SKIN PREPARATION, COSMETIC AND FOOD ADDITIVE

CROSS REFERENCE TO RELATED APPLICATIONS

This application is a National Stage of International Application No. PCT/JP2016/083942 filed Nov. 16, 2016, claiming priority based on Japanese Patent Application No. 2015-249020 filed Dec. 21, 2015.

TECHNICAL FIELD

The present invention relates to a novel nicotinamide mononucleotide derivative, a salt thereof, a method for producing the same, a topical skin preparation, a cosmetic and a food additive.

The present application claims priority on the basis of Japanese Patent Application No. 2015-249020, filed in Japan on Dec. 21, 2015, the contents of which are incorporated herein by reference.

BACKGROUND ART

Nicotinamide mononucleotide (abbreviated as "NMN") is an intermediate metabolite of the coenzyme, nicotinamide adenine dinucleotide ($NAD^+$).

$NAD^+$ is an electron carrier present in all living species. The correlation between $NAD^+$ and sirtuins, which are $NAD^+$-dependent deacetylases such as Sirt1 and Sirt3 and are involved in aging phenomena, has attracted attention in recent years. It is thought that aging phenomena can be inhibited by increasing intracellular $NAD^+$.

Antiaging action has also been observed for NMN, an intermediate metabolite of $NAD^+$, in the same manner as $NAD^+$ in dosing studies on mice (see, for example, Non-Patent Document 1). Therefore, utilization of the antiaging action of NMN is being examined in applications such as topical skin preparations, cosmetics and food additives.

However, NMN is a highly polar substance. Consequently, even if NMN is used as a material for topical skin preparations, adequate absorbability in the body is not obtained due to the inadequate skin permeability thereof. A method consisting of introducing a lipophilic functional group into NMN has been considered as a method for improving the skin permeability of NMN.

For example, Non-Patent Document 2 proposes a method for synthesizing a phosphodiester-type NMN, which is an NMN derivative having a lipophilic functional group. In addition, Non-Patent Document 2 indicates an example of synthesizing diacetyl NMN, a synthesis intermediate in which two hydroxyl groups of NMN are acetylated.

PRIOR ART DOCUMENTS

Patent Documents

Non-Patent Document 1: Cell Metab., 14, 528-536 (2011)
Non-Patent Document 2: Tetrahedron, 65, 8378-8383 (2009)

DISCLOSURE OF THE INVENTION

Problems to be Solved by the Invention

However, NMN derivatives of the prior art were unable to obtain adequate absorbability in the body. For example, since the acyl group of the diacetyl NMN described in Non-Patent Document 2 does not have adequate lipid solubility, it is unable to obtain adequate skin permeability, resulting in inadequate absorbability in the body. Consequently, the need arose to improve the absorbability of NMN derivatives in the body.

In addition, the phosphodiester-type NMN derivative described in Non-Patent Document 2 had the problem that after being absorbed through the skin, there is a difficulty in converting it into NMN, which is expected to demonstrate antiaging action.

In addition, in the case of using an NMN derivative as a material of a topical skin preparation, cosmetic or food additive, it is desirable that the NMN derivative has adequate water solubility so that it is applicable to various drug forms such as aqueous forms, emulsions, solids, powders or tablets.

With the foregoing in view, an object of the present invention is to provide an NMN derivative that is easily broken down into NMN in the body and has adequate lipid solubility and water solubility.

Means for Solving the Problems

The inventors of the present invention conducted extensive studies to solve the aforementioned problems.

As a result, the inventors of the present invention successfully developed a novel NMN derivative, and a salt thereof, in which an acyl group having 3 to 30 carbon atoms is introduced in place of the hydrogen atom of a hydroxyl group in one or both of the two hydroxyl groups present in the sugar backbone (furanose ring) of NMN. This novel NMN derivative, and salt thereof, is easily broken down into NMN in the body, has superior skin permeability due to its adequate lipid solubility, has high absorbability in the body, and in addition, it was confirmed to have adequate water solubility in the case of being used as a material of a topical skin preparation, cosmetic or food additive, thereby leading to completion of the present invention.

Namely, the present invention employs the configurations indicated below.

[1] A nicotinamide mononucleotide derivative, or salt thereof, which is a compound represented by general formula (1):

[Chemical Formula 1]

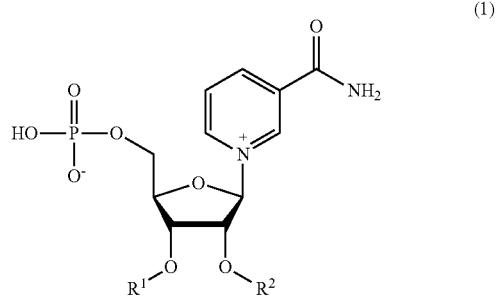

(wherein, $R^1$ and $R^2$ respectively and independently represent a hydrogen atom or an acyl group having 3 to 30 carbon atoms, a hydrocarbon group bound to a carbonyl carbon of the acyl group is a linear or branched, saturated or unsaturated hydrocarbon group, and at least one of $R^1$ and $R^2$ is the acyl group).

[2] The nicotinamide mononucleotide derivative, or salt thereof, described in [1], wherein $R^1$ and $R^2$ in the general formula (1) respectively and independently represent an acyl group having 6 to 16 carbon atoms.

[3] The nicotinamide mononucleotide derivative, or salt thereof, described in [1] or [2], wherein the salt of the compound of the general formula (1) is a salt formed with one or more types of anions selected from the group consisting of: nitrate ions, sulfate ions, carbonate ions, bicarbonate ions, halogen ions, formate ions, acetate ions, citrate ions, tartrate ions, oxalate ions, fumarate ions, anions of saturated or unsaturated fatty acids having 3 to 20 carbon atoms, anions of carnitine and derivatives thereof, anions of hydroxycitric acid and derivatives thereof, anions of ascorbic acid, and anions of ascorbyl phosphate and derivatives thereof.

[4] The nicotinamide mononucleotide derivative, or salt thereof, described in [1] or [2], wherein the salt of the compound of the general formula (1) is a salt formed with one or more types of cations selected from the group consisting of: sodium ions, potassium ions, calcium ions, magnesium ions, zinc ions, ammonium ions, and cations of carnitine and derivatives thereof.

[5] A method for producing the nicotinamide mononucleotide derivative, or salt thereof, described in any of [1] to [4], including: acylating nicotinamide mononucleotide using one or more types of acylating agents selected from the group consisting of: carboxylic acids having an acyl group having 3 to 30 carbon atoms, in which a linear or branched, saturated or unsaturated hydrocarbon group is bound to a carbonyl carbon; a halide of the carboxylic acid, and an anhydride of the carboxylic acid, in a solvent containing 20% by weight or more of a strongly acidic liquid having a pKa of 2.0 or less.

[6] The method for producing the nicotinamide mononucleotide derivative, or salt thereof, described in [5], wherein the strongly acidic liquid is trifluoroacetic acid or sulfuric acid.

[7] A topical skin preparation comprising the nicotinamide mononucleotide derivative, or a salt thereof, described in any of [1] to [4].

[8] A cosmetic comprising the topical skin preparation described in [7].

[9] A food additive comprising the nicotinamide mononucleotide derivative, or a salt thereof, described in any of [1] to [4].

Effects of the Invention

The NMN derivative or salt thereof of the present invention is easily broken down into NMN in the body and has adequate lipid solubility and water solubility. The NMN derivative or salt thereof of the present invention allows the obtaining of high absorbability in the body as a result of having adequate lipid solubility and is easily broken down into NMN in the body after having been absorbed into the body. Consequently, in the case of using it as a material of a topical skin preparation, cosmetic or food additive, for example, it can be expected to demonstrate potent antiaging action in comparison with the case of using an equal amount of NMN. In addition, the NMN derivative or salt thereof of the present invention has adequate lipid solubility and water solubility. Consequently, it can be used in a topical skin preparation, cosmetic or food additive in various forms, such as an aqueous form, emulsion, solid, powder or tablet.

BEST MODE FOR CARRYING OUT THE INVENTION

The following provides a detailed explanation of the nicotinamide mononucleotide derivative (NMN) or salt thereof of the present invention, a method for producing the same, and a topical skin preparation, cosmetic and food additive. The present invention is not limited to only the following examples, but can be applied in various ways within the scope of the claims.

1. NMN Derivative or Salt Thereof (NMN Derivative)

The NMN derivative of the present embodiment is a compound represented by the following general formula (1) (also abbreviated as "Compound (1)"):

[Chemical Formula 2]

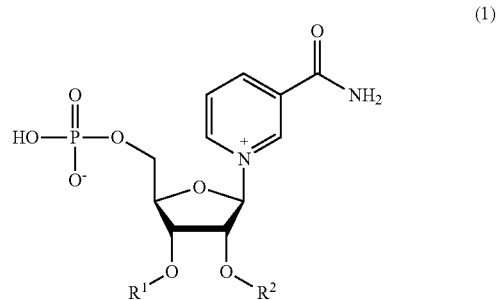

(1)

(wherein, $R^1$ and $R^2$ respectively and independently represent a hydrogen atom or acyl group having 3 to 30 carbon atoms, the hydrocarbon group bound to the carbonyl carbon of the acyl group is a linear or branched, saturated or unsaturated hydrocarbon group, and at least one of $R^1$ and $R^2$ is the acyl group).

The NMN derivative of the present invention is an inner salt in which an acid and base are present within a molecule thereof as represented by general formula (1).

At least one of $R^1$ and $R^2$ in general formula (1) represents an acyl group. Namely, this is equivalent to both $R^1$ and $R^2$ being the aforementioned acyl group, $R^1$ being the aforementioned acyl group and $R^2$ being a hydrogen atom, or $R^1$ being a hydrogen atom and $R^2$ being the aforementioned acyl group. In addition, in the case $R^1$ and $R^2$ both represent the aforementioned acyl group, $R^1$ and $R^2$ may be the same or different acyl groups.

$R^1$ and $R^2$ in general formula (1) respectively and independently represent a hydrogen atom or acyl group having 3 to 30 carbon atoms. The hydrocarbon group bound to the carbonyl carbon of the aforementioned acyl group (hydrocarbyl group) is a saturated or unsaturated hydrocarbon group having 2 to 29 carbon atoms. The saturated or unsaturated hydrocarbon group may be linear or branched.

Specific examples of the aforementioned saturated hydrocarbon group (alkyl group) include alkyl groups having 2 to 29 carbon atoms, such as an ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, heneicosyl group, docosyl group, tricosyl group, tetracosyl group, pentacosyl group, hexacosyl group, heptacosyl group, octacosyl group or nonacosyl group, as well as branched alkyl groups having the same number of carbon atoms as the aforementioned linear alkyl groups, such as a hexyldecyl group.

Examples of the aforementioned unsaturated hydrocarbon group include groups in which one or more of the single bonds (C—C) between carbon atoms contained in the alkyl groups indicated as examples of the aforementioned saturated hydrocarbon group is replaced by an unsaturated bond (double bond (C=C)) or triple bond (C≡C).

In the aforementioned unsaturated hydrocarbon group, the number of unsaturated bonds may be only one, or two or more. In the case the number of unsaturated bonds is two or more, all of the unsaturated double bonds may be double bonds or triple bonds, or there may be a mixture of double bonds and triple bonds in the unsaturated hydrocarbon group. There are no particular limitations on the position of the unsaturated bonds in the aforementioned unsaturated hydrocarbon group.

The number of unsaturated bonds in the aforementioned unsaturated hydrocarbon group is preferably 1 to 3 and more preferably 1 or 2. In addition, the aforementioned unsaturated hydrocarbon group preferably has only double bonds as the unsaturated bonds.

Preferable examples of the aforementioned unsaturated hydrocarbon group include alkenyl groups having 2 to 29 carbon atoms, such as an ethenyl group, propenyl group, butenyl group, pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, octadecenyl group, nonadecenyl group, eicosenyl group, heneicosenyl group, docosenyl group, tricosenyl group, tetracosenyl group, pentacosenyl group, hexacosenyl group, heptacosenyl group, octacosenyl group or nonacosenyl group, as well as branched alkenyl groups having the same number of carbon atoms as these linear alkenyl groups.

The aforementioned hydrocarbon group bound to the carbonyl carbon of the aforementioned acyl group is preferably an alkyl group or alkenyl group from the viewpoints of material availability and production cost.

In addition, the aforementioned hydrocarbon group bound to the carbonyl carbon of the aforementioned acyl group is preferably linear from the viewpoints of material availability and production cost.

The number of carbon atoms of the aforementioned acyl group represented by $R^1$ and $R^2$ is 3 to 30, preferably 4 to 24, more preferably 5 to 20, and particularly preferably 6 to 16. Namely, the number of carbons of the hydrocarbon group bound to the carbonyl carbon of the aforementioned acyl group is 2 to 29, preferably 3 to 23, more preferably 4 to 19, and particularly preferably 5 to 15.

If the number of carbon atoms of the acyl group is 3 or more (number of carbons of the hydrocarbon group is 2 or more), high absorbability in the body is obtained since adequate lipid solubility is obtained. In addition, if the number of carbon atoms of the acyl group is 30 or less (number of atoms of the hydrocarbon group is 29 or less), adequate water solubility is obtained.

(Salt of NMN Derivative)

A salt of the NMN derivative (salt of Compound (1)) of the present embodiment is a compound formed by an anion (or cation) derived from Compound (1) and a cation (or anion) derived from a compound other than Compound (1).

Examples of salts of Compound (1) include salts formed by a reaction between Compound (1) and an acid or base. These salts may be salts formed between Compound (1), functioning as a cation, and an anion, or salts formed between Compound (1), functioning as an anion, and a cation.

Examples of sites able to function as a cation moiety in Compound (1) include a nitrogen atom of the pyridine ring and a site (—$NH_3^+$) where a hydrogen ion ($H^+$) is coordinated with a nitrogen atom of the amino group represented by —$NH_2$.

On the other hand, examples of sites able to function as an anion moiety in Compound (1) include the phosphate group.

In addition, the cation and anion forming a salt of one molecule of Compound (1) may consist of only one cation and anion each or two or more cations and anions. In the case the number of cations and anions is two or more, all of these cations or anions may be the same or different, or only a portion thereof may be the same.

A salt of Compound (1) is preferably such that the entire molecule is electrically neutral, or in other words, such that the total valence of the cations contained in the salt of Compound (1) is equal to the total valence of the anions.

The anion that forms a salt of Compound (1) together with Compound (1) functioning as a cation may be an inorganic anion or organic anion. In addition, there are no particular limitations on the valence of the inorganic anion and organic anion, and may be, for example, a valence of 1 or a valence of 2 or more.

Preferable examples of inorganic anions include nitrate ions, sulfate ions, carbonate ions, bicarbonate ions and halogen ions. Examples of halogen ions include fluoride ions, chloride ions, bromide ions and iodide ions.

Preferable examples of organic anions include anions of carboxylic acid, anions of carnitine and derivatives thereof, anions of hydroxycitric acid and derivatives thereof, anions of ascorbic acid and anions of ascorbyl phosphate and derivatives thereof.

The aforementioned anions of carboxylic acid may be anions of a monocarboxylic acid (monovalent carboxylic acid) or anions of a polycarboxylic acid such as a dicarboxylic acid or tricarboxylic acid.

Examples of the aforementioned anions of carboxylic acid include anions of saturated or unsaturated fatty acids such as formate ions, acetate ions, propanoate (propionate) ions, butanoate (butyrate) ions, pentanoate (valerate) ions, hexanoate (caproate) ions, heptanoate (enanthate) ions, octanoate (caprylate) ions, nonanoate (pelargonate) ions, decanoate (caprate) ions, dodeconate (laurate) ions, tetradecanoate (myristate) ions, pentadecanoate ions, hexadecanoate (palmitate) ions, heptadeconate ions, octadecanoate (stearate) ions, eicosanoate (arachidate) ions, cis-9-octadecenoate (oleate) ions, cis,cis-9,12-octadecadienoate (linoleate) ions, cis,cis,cis-9,12,15-octadecatrienoate (α-linolenate) ions, all-cis-6,9,12-octadecatrienoate (γ-linolenate) ions or (5Z,8Z,11Z,14Z)-eicosa-5,8,11,14-tetraenoate (arachidonate) ions, anions of saturated or unsaturated dicarboxylic acids such as oxalate ions, malonate ions, succinate ions, glutarate ions, adipate ions, fumarate ions or maleate ions, and anions of hydroxy acids such as citrate ions, tartrate ions or hydroxycitrate ions.

Furthermore, in the present description, "fatty acid" refers to a monocarboxylic acid having a linear structure unless specifically indicated otherwise.

The number of carbon atoms of the aforementioned anions of saturated or unsaturated fatty acids is preferably 2 to 25 and more preferably 3 to 20. In addition, anions of unsaturated fatty acids preferably have 1 to 4 unsaturated bonds.

The number of carbon atoms of the aforementioned anions of saturated or unsaturated carboxylic acids is preferably 2 to 6 and more preferably 2 to 4. Anions of unsaturated carboxylic acids having two or more carbon atoms preferably have one unsaturated bond.

Among the aforementioned anions that form a salt of Compound (1) together with Compound (1) functioning as a cation, one or more types of anions selected from the group consisting of nitrate ions, sulfate ions, carbonate ions, bicarbonate ions, halogen ions, formate ions, acetate ions, citrate ions, tartrate ions, oxalate ions, fumarate ions, anions of saturated or unsaturated fatty acids having 3 to 20 carbon atoms, anions of carnitine and derivatives thereof, anions of hydroxycitric acid and derivatives thereof, anions of ascorbic acid and anions of ascorbyl phosphate and derivatives thereof are particularly preferable.

Cations that form a salt of Compound (1) together with Compound (1) functioning as an anion may be inorganic cations or organic cations. In addition, there are no particular limitations on the valence of the inorganic cations and organic cations, and they may have a valence of 1 or a valence of 2 or more.

Preferable examples of inorganic cations include sodium ions, potassium ions, calcium ions, magnesium ions, lithium ions, barium ions, aluminum ions, zinc ions, copper ions (including $Cu^+$ and $Cu^{2+}$ ions), iron ions (including $Fe^{2+}$ and $Fe^{3+}$ ions), manganese ions, nickel ions, tin ions (including $Sn^{2+}$ and $Sn^{4+}$ ions) and ammonium ions.

Preferable examples of organic cations include cations of carnitine and derivatives thereof.

Among the aforementioned cations that form a salt of Compound (1) together with Compound (1) functioning as an anion, one or more types of cations selected from the group consisting of sodium ions, potassium ions, calcium ions, magnesium ions, zinc ions, ammonium ions and cations of carnitine and derivatives thereof are particularly preferable.

Compound (1) and a salt of Compound (1) of the present embodiment may exist individually or may exist as a mixture of Compound (1) and a salt of Compound (1).

In addition, Compound (1) has a plurality of stereoisomers due to the presence of asymmetric atoms in a molecule thereof. Namely, all of these stereoisomers are included in Compound (1) and a salt thereof of the present embodiment (and these compounds may be collectively abbreviated as "Compound (1) or salt thereof"). More specifically, the Compound (1) or salt thereof may consist of an α-stereoisomer only or β-stereoisomer only, or may consist of a mixture of the α and β forms.

The Compound (1) or salt thereof of the present embodiment has suitable lipid solubility as a result of at least one of $R^1$ and $R^2$ in general formula (1) being an acyl group having 3 or more carbon atoms. Consequently, Compound (1) or salt thereof demonstrates superior skin affinity and skin permeability, and has higher absorbability in the body (percutaneous absorbability), than NMN, conventional NMN derivatives and salts thereof. Moreover, Compound (1) or salt thereof of the present embodiment is easily broken down by biological enzyme reactions in the body after having been absorbed into the body, thereby resulting in NMN, which can be expected to demonstrate antiaging action. Thus, a topical skin preparation or cosmetic containing the Compound (1) or salt thereof, for example, enables a remarkably large amount of NMN to reach the skin tissue in comparison with the case of it containing NMN, conventional NMN derivatives and salts thereof.

In addition, despite having adequate lipid solubility, Compound (1) or salt thereof has adequate water solubility in the case of using as a material of, for example, a topical skin preparation, cosmetic or food additive, as a result of at least one of $R^1$ and $R^2$ in general formula (1) being an acyl group having 30 or less carbon atoms. Consequently, Compound (1) or salt thereof demonstrates superior handling ease, can be easily incorporated in a topical skin preparation, cosmetic or food additive, and can be used in topical skin preparations, cosmetics and food additives in various forms such as an aqueous form, emulsion, solid, powder or tablet. Accordingly, Compound (1) or salt thereof is useful as a material of a topical skin preparation, cosmetic or food additive.

2. Method for Producing NMN Derivative or Salt Thereof

In the method for producing Compound (1) or salt thereof of the present embodiment, NMN is acylated using an acylating agent in a solvent containing 20% by weight or more of a strongly acidic liquid having a pKa of 2.0 or less.

In the present embodiment, the NMN used as raw material may consist of an α-stereoisomer or β-stereoisomer only, or may consist of a mixture of the α and β forms.

In the present embodiment, a solvent containing 20% by weight or more of a strongly acidic liquid having a pKa of 2.0 or less is used. A solvent that is a liquid at 25° C. is used as the strongly acidic liquid. A polyvalent acid such as sulfuric acid can have a plurality of pKa values. In the case the solvent has a plurality of pKa values, the lowest pKa value is used in the present invention.

The following provides a detailed explanation of pKa.

The acid dissociation constant, pKa, is a parameter that indicates the degree of dissociation of an acid. If the ionization constant of an acid is taken to be Ka, then pKa is defined as $-\log_{10}$ Ka. It means that the lower the pKa value, the stronger the acid strength. pKa is normally measured in water at 25° C. using a method such as potentiometric titration, UV-visible spectroscopy or nuclear magnetic resonance spectroscopy.

However, the pKa of extremely strong acids such as hydrochloric acid and sulfuric acid cannot be measured accurately in water due to a leveling effect attributable to the solvent. The leveling effect refers to a phenomenon by which, when the pKa of an acid that is stronger than oxonium ion ($H_3O^+$, pKa=−1.7) is attempted to be measured in water, the acid completely reacts with water and ends up reflecting the acid strength of the oxonium ion, thereby resulting in an apparent leveling of the strength of the acid. Thus, in order to compare the strengths of extremely strong acids, it is necessary to either compare pKa values measured in organic solvents such as acetic acid, dimethylsulfoxide and acetonitrile, which have a higher proton donating ability than water, or compare values determined with the Hammett acidity function. Although the pKa values of acids such as hydrochloric acid and sulfuric acid in water are indicated in the literature, these are estimated values based on results obtained by measuring in an organic solvent that were subsequently converted to values in water.

The strongly acidic liquid having a pKa of 2.0 or less of the present embodiment is a liquid having a pKa value of 2.0 or less in water. In the present embodiment, a liquid that corresponds to a liquid having a pKa of 2.0 or less is that for which the measured value of pKa in water is 2.0 or less, that for which acidity is too strong to be measured in water, or that for which pKa in water has been determined to be 2.0 or less by converting the measurement results carried out in an organic solvent.

In the present embodiment, since the pKa of the strongly acidic liquid is 2.0 or less, NMN can be adequately dissolved in the solvent. As a result, NMN can be acylated efficiently and Compound (1) is obtained at a high yield. The pKa of the strongly acidic liquid is preferably 1.5 or less and more preferably 1.0 or less.

Specific examples of strongly acidic liquids having a pKa of 2.0 or less include trifluoroacetic acid, difluoroacetic acid, dichloroacetic acid, pentafluoropropionic acid, heptafluorobutyric acid, perfluoropentanoic acid, perfluorohexanoic acid, sulfuric acid, methanesulfonic acid, ethanesulfonic acid and trifluoromethanesulfonic acid. Among these, trifluoroacetic acid, sulfuric acid, methanesulfonic acid or trifluoromethanesulfonic acid is used preferably from the viewpoint of cost.

One type of the aforementioned strongly acidic liquid may be used alone or two or more types of the strongly acidic liquids may be used in combination. In the case of using two or more types in combination, the combination and ratio thereof can be suitably selected according to the objective.

In the present embodiment, a solvent consisting of a mixture of a strongly acidic liquid and another organic solvent may be used as the solvent. There are no particular limitations on the other solvent mixed with the strongly acidic liquid provided it does not react with NMN and does not decompose in acid. Specific examples of these other organic solvents include dichloromethane, chloroform, 1,2-dichloroethane, toluene, benzene, dimethylsulfoxide, N,N-dimethylformamide and acetonitrile.

The ratio of the strongly acidic liquid in the solvent is 20% by weight to 100% by weight. If the content of the strongly acidic liquid in the solvent is 20% by weight or more, NMN can be adequately dissolved in the solvent, thereby enabling NMN to be acylated efficiently and allowing the production of Compound (1) or salt thereof at a high yield. The content of the strongly acidic liquid in the solvent is preferably 50% by weight to 100% by weight and more preferably 80% by weight to 100% by weight from the viewpoint of NMN solubility. If the content of the strongly acidic liquid in the solvent is 100% by weight, it means that the strongly acidic liquid per se is used as the solvent.

There are no particular limitations on the amount of solvent used relative to the amount of NMN used as raw material, and may be suitably selected in consideration of such factors as the solubility of NMN in the solvent or stirring ease of the reaction liquid.

In the present embodiment, a carboxylic acid having an acyl group having 3 to 30 carbon atoms in which a linear or branched, saturated or unsaturated hydrocarbon group is bound to the carbonyl carbon, a halide of the aforementioned carboxylic acid, or an anhydride of the aforementioned carboxylic acid, is used as an acylating agent. A hydrochloride or bromide is preferably used as the acylating agent in the case of using a halide of the aforementioned carboxylic acid.

Among the aforementioned acylating agents, a carboxylic acid chloride (acid chloride) such as palmitoyl chloride ($CH_3(CH_2)_{14}COCl$), lauroyl chloride ($CH_3(CH_2)_{10}COCl$), octanoyl chloride ($CH_3(CH_2)_6COCl$) or hexanoyl chloride ($CH_3(CH_2)_4COCl$) is particularly preferable for use as the acylating agent since it allows the production at a high yield.

One type of these acylating agents may be used alone or two or more types may be used in combination. In the case of using two or more types of acylating agents in combination, the combination and ratio thereof can be suitably selected according to the objective.

The amount of acylating agent used relative to the amount of NMN used as raw material can be suitably adjusted according to such factors as the type of target product (type of acylating agent) or type of solvent. The two hydroxyl groups present in the sugar backbone (furanose ring) of NMN are at the 3' position and 2' position. If NMN is acylated using the method of the present embodiment, a compound in which the hydroxyl group at the 3' position of the sugar backbone is acylated, a compound in which the hydroxyl group at the 2' position of the sugar backbone is acylated, and a compound in which both the hydroxyl groups at the 3' position and 2' position are acylated, are produced. In the present embodiment, the ratio of these products can be altered as indicated below by adjusting the amount of acylating agent used relative to the amount of NMN used.

The reactivity of the acylation reaction differs between the hydroxyl group at the 2' position and the hydroxyl group at the 3' position of the sugar backbone of NMN. The reactivity of the acylation reaction is higher for the hydroxyl group at the 3' position than the hydroxyl group at the 2' position. Consequently, if the amount of acylating agent used is low relative to the amount of NMN, a product in which only the hydroxyl group at the 3' position of the sugar backbone (product in which $R^1$ represents an acyl group and $R^2$ represents a hydrogen atom in general formula (1)) is easily produced. In addition, if the amount of acylating agent used is high relative to the amount of NMN, a product in which not only the hydroxyl group at the 3' position, but also the hydroxyl group at the 2' position, of the sugar backbone (product in which $R^1$ and $R^2$ represent acyl groups in general formula (1)) is easily produced. In addition, a product in which only the hydroxyl group at the 2' position of the sugar backbone is acylated (product in which $R^1$ represents a hydrogen atom and $R^2$ represents an acyl group in chemical formula (1)) is never produced in the largest amount regardless of the amount of acylating agent used relative to the amount of NMN.

More specifically, in the case of using, for example, an acid chloride as the acylating agent and using trifluoroacetic acid as the solvent, if the acid chloride is used in an amount equal to 0.5 to 2 times the number of moles of NMN, a product in which only the hydroxyl group at the 3' position of the sugar backbone is acylated is produced in the largest amount. In addition, if the acid chloride is used in an amount equal to 2.5 times or more the number of moles of NMN, a product in which both the hydroxyl groups at the 2' position and 3' position of the sugar backbone are acylated is produced in the largest amount.

In addition, different types of acyl groups can be introduced for $R^1$ and $R^2$ in Compound (1) or salt thereof by utilizing the difference in reactivity between the hydroxyl groups at the 2' position and 3' position of the sugar backbone. Namely, the hydroxyl group at the 3' position of the sugar backbone is acylated first using a low amount of acylating agent relative to NMN. Subsequently, a different type of acylating agent is added to acylate a hydroxyl group of the sugar backbone that has not been acylated. As a result, Compound (1) or salt thereof is produced in which different types of acyl groups are introduced for $R^1$ and $R^2$. In this case, it is preferable to suitably adjust the amount of the acylating agent used first by monitoring the progress of the acylation reaction.

Although there are no particular limitations on the reaction temperature of the acylation reaction, it is preferably −20° C. to 50° C. and more preferably 0° C. to 30° C. Since NMN is a compound that is easily decomposed by heating, the temperature of the acylation reaction is preferably 50° C. or lower. Since the acylation reaction progresses slowly and reaction time becomes excessively long if the reaction temperature is too low, the temperature of the acylation reaction is preferably −20° C. or higher.

In addition, although there are no particular limitations on the duration of the acylation reaction, it is preferably 0.5 hours to 24 hours and more preferably 0.5 hours to 12 hours.

Compound (1) or salt thereof produced by the acylation reaction can be subjected to post-treatment according to a known method as necessary following completion of the acylation reaction, and the target Compound (1) or salt thereof can be extracted according to a known method.

As post-treatment following the acylation reaction, any post-treatment such as filtration, washing, extraction, pH adjustment, dehydration or concentration can be carried out, either alone or as a combination of two or more types thereof, on the reaction liquid obtained following completion of the acylation reaction. In addition, the target Compound (1) or salt thereof can be extracted from the product following post-treatment by a method such as concentration, crystallization, re-precipitation or column chromatography.

The extracted Compound (1) or salt thereof can be purified by further carrying out one or more rounds of a procedure such as crystallization, re-precipitation, column chromatography, extraction or stirring and washing of crystals with solvent as necessary, either alone or by combining two or more types thereof.

In addition, the Compound (1) or salt thereof produced by the acylation reaction can be used successively in a target application without being extracted after post-treatment carried out as necessary on the resulting reaction liquid following completion of the acylation reaction.

Furthermore, there are cases in which all of the target product obtained according to the aforementioned production method is in the form of an inner salt in which both acid and base are present within a molecule of Compound (1) or salt thereof, as well as cases in which acid and base are not present within a molecule of the Compound (1) or salt thereof in all or a portion of the target product. In addition, there are also cases in which all or a portion of the target product obtained according to the aforementioned production method is the Compound (1) or salt thereof formed by an anion (or cation) derived from Compound (1) and a cation (or anion) derived from a compound other than Compound (1).

In addition, a salt of Compound (1) may be produced according to the following method. Namely, the Compound (1) or salt thereof produced according to the aforementioned acylation reaction is treated with an excess amount of acid or base and the Compound (1) or salt thereof is reacted with the acid or base. The resulting salt of Compound (1) can then be extracted using the same method as that used for the aforementioned Compound (1) or salt thereof.

In addition, a salt of Compound (1) may also be produced by extracting Compound (1) or a salt thereof produced according to the aforementioned production method, followed by treating the extracted Compound (1) or salt thereof with an excess amount of acid or base, and then reacting Compound (1) or salt thereof with acid or base. In this case as well, the resulting salt of Compound (1) can be extracted using the same method as that used for the aforementioned Compound (1) or salt thereof.

The structure of the Compound (1) or salt thereof obtained in the present embodiment can be confirmed by a known method such as nuclear magnetic resonance (NMR), mass spectroscopy (MS), infrared spectroscopy (IR) or UV-visible spectroscopy (UV-VIS absorption spectroscopy).

In the method for producing the Compound (1) or salt thereof of the present embodiment, NMN is acylated using one or more types of acylating agents selected from the group consisting of a carboxylic acid having 3 to 30 carbon atoms in which a linear or branched, saturated or unsaturated hydrocarbon group is bound to the carbonyl carbon, a halide of the aforementioned carboxylic acid, and an anhydride of the aforementioned carboxylic acid, in a solvent containing 20% by weight or more of a strongly acidic liquid having a pKa of 2.0 or less. Consequently, Compound (1) or salt thereof of the present embodiment, which is easily broken down into NMN in the body, has adequate lipid solubility, and has adequate water solubility in the case of using it as a material of a topical skin preparation, cosmetic or food additive, can be produced.

In general, in the case of acylating an alcohol, the alcohol is first dissolved in an organic solvent such as dichloromethane, toluene or N,N-dimethylformamide, and then reacted with a carboxylic acid chloride or carboxylic acid anhydride in the presence of a base such as triethylamine, pyridine, N-methylmorpholine or 4-dimethylaminopyridine.

The NMN used as raw material in the present embodiment does not dissolve in ordinary organic solvents. Consequently, NMN is hardly acylated at all under ordinary conditions used in the case of acylating an alcohol. In addition, NMN decomposes if heated for the purpose of dissolving in an organic solvent.

In contrast, in the production method of the present embodiment, a solvent containing 20% by weight or more of a strongly acidic liquid having a pKa of 2.0 or less is used as the solvent. Thus, NMN can be dissolved in the solvent without causing decomposition thereof, thereby enabling NMN to be acylated efficiently.

3. Topical Skin Preparation and Cosmetic

The topical skin preparation of the present embodiment contains the previously described Compound (1) or salt thereof of the present embodiment. In addition, the cosmetic of the present embodiment contains the topical skin preparation of the present embodiment. The topical skin preparation of the present embodiment can also be used as a cosmetic.

Examples of the aforementioned topical skin preparation and cosmetic include hair cosmetics such as shampoos, oil-based shampoos, creamy shampoos, conditioning shampoos, dandruff shampoos, hair coloring shampoos, conditioner-containing shampoos, hair conditioners, hair treatment agents, hair packs, hair foams, hair mousse, hair sprays, hair mists, hair wax, hair gels, water-based hair styling creams, hair setting lotions, coloring lotions, hair tonics, hair liquids, pomade, hair oil sticks, hair creams, blow drying treatment agents, split end coating treatment agents, hair oils, permanent wave agents, hair straighteners, oxidative hair dyes, hair bleaches, hair color pre-treatment agents, hair color after-treatment agents, permanent wave pre-treatment agents, permanent wave after-treatment agents, hair manicures or hair growth agents; foundation cosmetics such as facial washes, cleaning foams, cleansing powders, face washing powders, cleansing creams, cleansing milky lotions, cleansing lotions, cleansing gels, cleansing oils, cleansing facial masks, beauty washes, moisturizers, astringents, cleansing washes, multilayered beauty washes, milky liquids, emollient lotions, moisturizing lotions, milky lotions, nourishing lotions, nourishing milky lotions, skin moisturizers, moisturizing emulsions, massage lotions, cleansing lotions, protective emulsions, sun blocks, sun protectors, UV-protective milky lotions, sunscreens, makeup lotions, corneal smoothening agents, elbow lotions, hand lotions, body lotions, creams, emollient creams, nutrient creams, nourishing creams, vanishing creams, moisturizing creams, night creams, massage creams, cleansing creams, makeup creams, base creams, pre-makeup creams, sunscreen creams, suntan creams, depilatory creams, deodorant creams, shaving creams, corneal softening creams, gels, cleansing gels, moisturizing gels, soap, face soaps, clear soaps, medicinal soaps, liquid soaps, shaving soaps, synthetic face soaps, facial packs, facial masks, peel-off facial masks, powder facial packs, washing facial packs, oil facial packs, cleansing facial masks, essences, moisturizing essences, whitening essences, UV-protective essences, liposome essences or liposome beauty washes; makeup cosmetics such as face powder/dusting powder, foundations, makeup bases, lipsticks, lip gloss, rouge, eye liners, mascara, eye shadow, eyebrow pencils, eye brow coloring agents, nail enamel, enamel remover or nail treatment agents; fragrant cosmetics such as cologne, perfumes, parfums, eau de parfums, eau de toilettes, eau de colognes, solid perfumes, fragrant powders, fragrant soaps, body lotions or bath oils; body cosmetics such as body shampoos, body cleansers, body powders, deodorant lotions, deodorant powders, deodorant sprays, stick deodorants, deodorant cosmetics, bleaching agents, depilatory agents/hair removal agents, bath additives, insect repellent sprays or insect repellents; as well as ointments, patches, lotions, liniments and liquid coating agents.

Examples of forms of the aforementioned topical skin preparations and cosmetics include emulsions such as oil-in-water (O/W), water-in-oil (W/O), W/O/W or O/W/O emulsions, emulsion polymers, oils, solids, liquids, pasty solids, sticks, essential oils, powders, jellies, gels, pastes, creams, sheets, films, mists, sprays, multilayered products, foams and flakes.

The aforementioned topical skin preparation and cosmetic contain one or more types of essential ingredients selected from the group consisting of Compound (1) and salts thereof. Thus, the aforementioned topical skin preparation and cosmetic may contain Compound (1) but not contain a salt of Compound (1), may contain a salt of Compound (1) but not contain Compound (1), or may contain both Compound (1) and a salt of Compound (1).

One type of Compound (1) or two or more types of Compound (1) may be contained in the aforementioned topical skin preparation and cosmetic. In the case of containing two or more types of Compound (1), the combination and ratios thereof can be suitably selected according to the objective. Similarly, one type of a salt of Compound (1) or two or more types of a salt of Compound (1) may be contained in the aforementioned topical skin preparation and cosmetic. In the case of containing two or more types of a salt of Compound (1), the combination and ratios thereof can be suitably selected according to the objective.

In addition to Compound (1) or a salt thereof, the aforementioned topical skin preparation and cosmetic may also contain other ingredients such as ingredients ordinarily used in topical skin preparations or cosmetics at a typical concentration, such as 100 ppm by weight to 90% by weight based on the total weight of the topical skin preparation or cosmetic, as necessary within a range that does not impair the effects of the present invention.

Examples of ingredients ordinarily used in topical skin preparations or cosmetics include ingredients such as raw materials listed in existing raw material standards or official compendia, and carriers or additives pharmaceutically acceptable as topical skin preparations.

Examples of raw materials listed in existing raw material standards or official compendia include those listed in the 14th edition of the Japanese Pharmacopoeia (Pharmaceutical and Medical Device Regulatory Science Society of Japan, ed., Jiho, Inc., pub., April 2001), Japanese Standards of Cosmetic Ingredients with Commentary, 2nd edition (Pharmaceutical and Medical Device Regulatory Science Society of Japan, ed., Yakuji Nippo Ltd., pub., 1984), Japanese Cosmetic Ingredients Codex (Ministry of Health, Labour and Welfare, Pharmaceutical Affairs Bureau, Evaluation and Registration Division, supervisor, Yakuji Nippo Ltd., pub., 1993), Supplement to the Japanese Cosmetic Ingredients Codex (Ministry of Health, Labour and Welfare, Pharmaceutical Affairs Bureau, Evaluation and Registration Division, supervisor, Yakuji Nippo Ltd., pub., 1993), Japanese Cosmetic Classification Permission Standards (Ministry of Health, Labour and Welfare, Pharmaceutical Affairs Bureau, Evaluation and Registration Division, supervisor, Yakuji Nippo Ltd., pub., 1993), International Cosmetic Ingredient Dictionary and Handbook 2002 (Ninth Edition, Vol. 1-4, CTFA, pub.), and the Encyclopedia of Cosmetic Ingredients (Nikko Chemicals Co., Ltd., pub., 1991).

Examples of pharmaceutically acceptable ingredients of topical skin preparations include water and the hydrocarbons, natural oils and fats, fatty acids, higher alcohols, alkyl glyceryl ethers, esters, silicone oils, polyvalent alcohols, monovalent lower alcohols, sugars, polymers, anionic surfactants, cationic surfactants, amphoteric surfactants, non-ionic surfactants, natural surfactants, UV absorbers, powders, colorants, amino acids, peptides, vitamins, vitamin-like agents, preservatives, antioxidants, metal ion chelating agents, moisturizers, anti-inflammatory agents, pH adjusters, salts, organic acids, whitening agents, refined oils, terpenes and fragrances described in paragraphs 0018 to 0050 of Japanese Unexamined Patent Application, First Publication No. 2012-236800.

One type of these other ingredients may be used alone or two or more types may be used in combination. In the case of using two or more types in combination, the combination and ratios thereof can be suitably selected according to the objective.

The total content of the aforementioned Compound (1) and salts thereof in the topical skin preparation and cosmetic of the present embodiment (content of essential ingredients) is preferably 0.01% by weight to 20% by weight, more preferably 0.05% by weight to 12% by weight, and particularly preferably 0.1% by weight to 10% by weight. If the total content of Compound (1) and salts thereof is equal to or greater than the aforementioned lower limit value, anti-aging action of Compound (1) and salts thereof is easily obtained, and superior efficacy as a topical skin preparation or cosmetic is obtained. In addition, if the total content of Compound (1) and salts thereof is equal to or less than the aforementioned upper limit value, excess use of these ingredients can be inhibited.

Although the dosage of the topical skin preparation of the present invention cannot be uniformly defined since it differs according to such factors as the symptoms, body weight, age or sex of the patient, normally the adult daily dosage is preferably an amount such that the dosage of the active ingredient (total dosage of Compound (1) and salts thereof) is 0.4 mg/person to 400 mg/person.

A prescribed amount of the aforementioned topical skin preparation is administered once a day or divided among multiple administrations per day.

Since the topical skin preparation of the present embodiment contains Compound (1) or a salt thereof having high absorbability in the body, the dosage of the active ingredient (total dosage of Compound (1) and salts thereof) can be reduced in comparison with the case of using NMN as the active ingredient.

In addition, although the amount used of the cosmetic of the present embodiment cannot be uniformly defined since it varies according to such factors as the symptoms, body weight, age or sex of the user, normally the amount of active ingredient used (total amount used of Compound (1) and salts thereof) per day by an adult is preferably 0.4 mg/person to 400 mg/person.

A prescribed amount of the aforementioned cosmetic is used once a day or divided among multiple uses per day.

Since the cosmetic of the present embodiment contains Compound (1) or a salt thereof having high absorbability in the body, the amount of active ingredient used (total amount used of Compound (1) and salts thereof) can be reduced in comparison with the case of using NMN as the active ingredient.

The aforementioned topical skin preparation and cosmetic can be produced by incorporating and formulating Compound (1) or a salt thereof and other ingredients as necessary.

The aforementioned topical skin preparation and cosmetic can be produced using the same method as known topical skin preparations and cosmetics with the exception of incorporating Compound (1) or a salt thereof.

The topical skin preparation and cosmetic of the present embodiment contains Compound (1) or salt thereof that is easily broken down to NMN in the body, has superior skin affinity and skin permeability, and has high absorbability in the body. Thus, the topical skin preparation and cosmetic of the present embodiment can be expected to demonstrate potent antiaging action. The topical skin preparation and cosmetic of the present embodiment is particularly useful as a sebum control agent, skin turnover normalization agent, anti-inflammatory agent, anti-acne agent, anti-rough skin agent, gray hair inhibitor, topical hair growth agent or antiaging agent. In addition, since the topical skin preparation and cosmetic of the present embodiment contains Compound (1) or salt thereof having adequate lipid solubility and water solubility, it can be prepared in various forms such as an aqueous form, emulsion, solid, powder or tablet.

4. Food Additive

The food additive of the present embodiment contains the previously described Compound (1) or a salt thereof of the present embodiment. The food additive of the present embodiment contains one or more types of essential ingredients selected from the group consisting of Compound (1) and salts thereof in the same manner as the previously described topical skin preparation and cosmetic of the present embodiment. Thus, the aforementioned food additive may contain Compound (1) but not contain a salt of Compound (1), may contain a salt of Compound (1) but not contain Compound (1), or may contain both Compound (1) and a salt of Compound (1).

Only one type of Compound (1) may be contained in the aforementioned food additive or two or more types may be contained. In the case of containing two or more types, the combination and ratios thereof can be suitably selected according to the objective. Similarly, only one type of salt of Compound (1) may be contained in the aforementioned food additive or two or more types may be contained. In the case of containing two or more types, the combination and ratios thereof can be suitably selected according to the objective.

In addition to Compound (1) or a salt thereof, the aforementioned food additive may also contain arbitrary ingredients known in the art as necessary. There are no particular limitations on these arbitrary ingredients, and can be suitably selected according to the objective. One type of arbitrary ingredient may be used or two or more types may be used in combination. In the case of using two or more types in combination, the combination and ratios thereof can be suitably selected according to the objective. There are no particular limitations on the content of arbitrary ingredients in the aforementioned food additive, and can be suitably adjusted according to the objective.

There are no particular limitations on the total content of Compound (1) and salts thereof (total amount of essential ingredients) in the aforementioned food additive, and although the content is suitably adjusted according to the objective, normally the content is preferably 0.001% by weight to 0.1% by weight.

Although the amount of the food additive of the present embodiment used cannot be uniformly defined since the amount used varies according to the objective, normally the amount used per day by an adult is an amount such that the ingested amount of active ingredient (total ingested amount of Compound (1) and salts thereof) is 10 mg/person to 1000 mg/person.

The aforementioned food additive can be produced using the same method as known food additives with the exception of incorporating Compound (1) or a salt thereof.

The food additive of the present embodiment contains Compound (1) or salt thereof that is easily broken down to NMN in the body and has high absorbability in the body. Thus, the food additive of the present embodiment can be expected to demonstrate potent antiaging action. In addition, since the food additive of the present embodiment contains Compound (1) or salt thereof having adequate lipid solubility and water solubility, it can be prepared in various forms such as a tablet, coated tablet, pill, powder, granules, capsule, liquid, suspension or emulsion in the same manner as known food additives.

EXAMPLES

The following provides a more detailed explanation of the present invention through examples thereof. Furthermore, the present invention is not limited to the examples indicated below.

The reagents indicated below were used as raw materials in the examples and comparative examples indicated below.

β-nicotinamide mononucleotide (β-NMN): Sigma-Aldrich Co. LLC

Trifluoroacetic acid (TFA): Tokyo Chemical Industry Co., Ltd.

Sulfuric acid: Junsei Chemical Co., Ltd.

Palmitoyl chloride (PaCl ($CH_3(CH_2)_{14}COCl$): Tokyo Chemical Industry Co., Ltd.

Lauroyl chloride (LauCl ($CH_3(CH_2)_{10}COCl$): Tokyo Chemical Industry Co., Ltd.

Octanoyl chloride (OctCl ($CH_3(CH_2)_6COCl$): Tokyo Chemical Industry Co., Ltd.

Hexanoyl chloride (HexCl ($CH_3(CH_2)_4COCl$): Tokyo Chemical Industry Co., Ltd.

Palmitic acid (PaOH ($CH_3(CH_2)_{14}COOH$): Tokyo Chemical Industry Co., Ltd.

Acetic anhydride: Tokyo Chemical Industry Co., Ltd.

Pyridine (anhydrous): Wako Pure Chemical Industries, Ltd.

Hexane: Wako Pure Chemical Industries, Ltd.

Acetonitrile: Wako Pure Chemical Industries, Ltd.

N,N-dimethylformamide (anhydrous) (DMF): Wako Pure Chemical Industries, Ltd.

In addition, in each of the following examples, comparative examples and synthesis examples, quantification of the target compound in the form of an NMN derivative and palmitic acid was carried out by analyzing with HPLC (high-performance liquid chromatography) under HPLC Analysis Conditions 1 indicated below, while quantification of the raw material (β-NMN) was carried out by analyzing with HPLC under HPLC Analysis Conditions 2 indicated below.

[HPLC Analysis Conditions 1]

Column: Shodex® Silica 5C8 4E (Showa Denko K.K.), 4.6 mm I.D.×250 mm, 2 columns

Eluent: $H_3PO_4$, $KH_2PO_4$ aqueous solution ($H_3PO_4$ concentration: 15 mmol/L, $KH_2PO_4$ concentration: 15 mmol/L)/acetonitrile=30/70 (volume ratio)

Flow rate: 1.2 mL/min

Column temperature: 40° C.

Detector: UV (210 nm) and RI (differential refractometer)

Sample injection volume: 20 μL

[HPLC Analysis Conditions 2]

Column: Shodex® RSpak® DM-614 (Showa Denko K.K.), 6.0 mm I.D.×150 mm, 4 columns

Eluent: 0.02% aqueous $H_3PO_4$ solution

Flow rate: 0.8 mL/min

Column temperature: 40° C.

Detector: UV (210 nm) and RI (differential refractometer)

Sample injection volume: 20 μL

In addition, in each of the following examples, comparative examples and synthesis examples, structures of the products were identified by NMR measurement. NMR measurement was carried out using the Avance III-400 (Bruker Biospin GmbH) by measuring samples obtained by dissolving about 15 mg of the sample targeted for measurement in various deuterated solvents.

Production of Compounds

Example 1

Synthesis of 3'-Palmitoyl-β-NMN in TFA Solvent

[Chemical Formula 3]

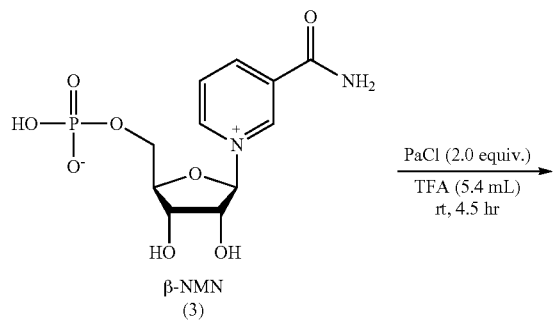

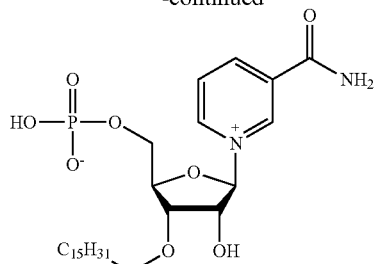

3'-Palmitoyl-β-NMN
56%
(3-1)

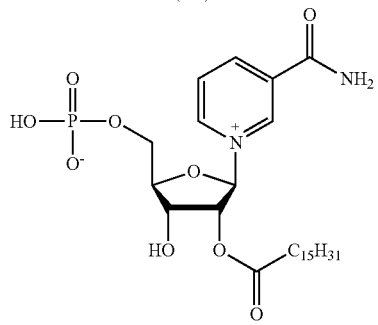

2'-Palmitoyl-β-NMN
9%
(3-2)

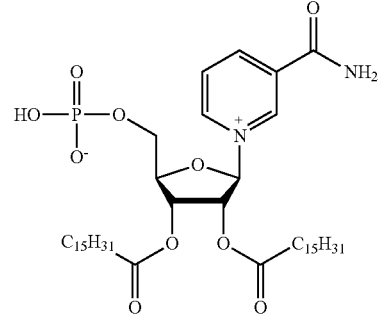

2', 3'-Dipalmitoyl-β-NMN
6%
(3-3)

The β-nicotinamide mononucleotide (β-NMN, 0.133 g, 0.40 mmol) represented by general formula (3) above was added to trifluoroacetic acid (TFA, 5.4 mL, pKa=−0.25), which is a strongly acidic liquid, and dissolved completely followed by adding palmitoyl chloride (PaCl, 0.110 g, 0.40 mmol) as an acylating agent at room temperature (23° C.) and stirring for 1 hour. Subsequently, additional palmitoyl chloride (PaCl, 0.110 g, 0.40 mmol) was added followed by additionally stirring for 3.5 hours and acylating for a total of 4.5 hours.

Following completion of the acylation reaction, a portion of the resulting reaction liquid was sampled followed by quantifying the product under HPLC Analysis Conditions 1 and then quantifying the raw material under HPLC Analysis Conditions 2 to determine the respective conversion rates and yields of the compounds represented by general formulas (3-1) to (3-3) above. The results are shown in Table 1.

Following completion of the acylation reaction, the reaction liquid was subjected to post-treatment in the form of concentration and drying (removal of TFA), and after adding 20 mL of hexane and 20 mL of acetonitrile and stirring, the undissolved white solid that remained was recovered by filtration (removal of palmitic acid and residual TFA) and 10 mL of water were added to the recovered white solid and stirred followed by recovering the undissolved white solid that remained in the same way (removal of NMN). The recovered white solid (product) was then purified by combining column chromatography (silica gel and ion exchange resin) to obtain the target compound, 3'-palmitoyl-β-nicotinamide mononucleotide (3'-palmitoyl-β-NMN) represented by the aforementioned general formula (3-1), as the main component in the form of a white solid (0.061 g, isolated yield: 27%).

Table 1 shows the acylating agent used, molar ratio of acylating agent to NMN (acylating agent/NMN), solvent and isolated yield of the main component in Example 1.

The structure of the target compound was confirmed by carrying out various NMR measurements ($^1$H-NMR, $^{13}$C-NMR, $^{13}$C-DEPT135 and $^1$H-$^1$H-COSY). In addition, the target compound was confirmed to have not undergone epimerization based on the chemical shift of the proton at the 1' position of the sugar backbone and the structure of β-NMN was determined to have been retained.

The $^1$H-NMR and $^{13}$C-NMR data of the resulting 3'-palmitoyl-β-NMN are indicated below.

$^1$H-NMR (400 MHz, THF-ds/D$_2$O=5/1): δ (ppm)=9.50 (s, 1H), 9.29 (d, J=8.0 Hz, 1H), 9.02 (d, J=8.0 Hz, 1H), 8.37 (dd, J=8.0 and 8.0 Hz, 1H), 6.11 (d, J=4.0 Hz, 1H), 5.43 (d, J=4.0 Hz, 1H), 4.78 (dd, J=4.0 and 4.0 Hz, 1H), 4.59 (m, 1H), 4.06-4.31 (m, 2H), 2.44 (m, 2H), 1.61 (m, 2H), 1.25 (m, 24H), 0.85 (t, J=4.0 Hz, 3H)

$^{13}$C-NMR (100 MHz, THF-ds/D$_2$O=5/1): δ (ppm)=173.8, 165.5, 147.3, 143.6, 140.6, 135.5, 129.8, 101.2, 87.7, 77.5, 75.7, 65.4, 34.6, 32.8, 30.1-30.6, 23.5, 14.5

Example 2

Synthesis of 2',3'-Dipalmitoyl-β-NMN in TFA Solvent

[Chemical Formula 4]

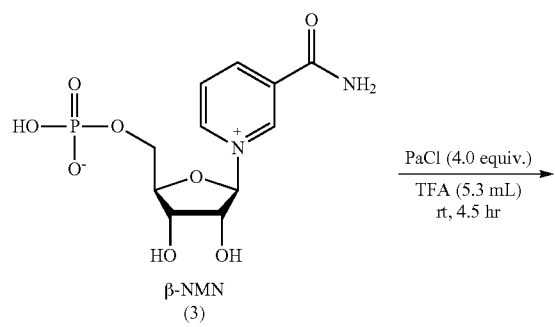

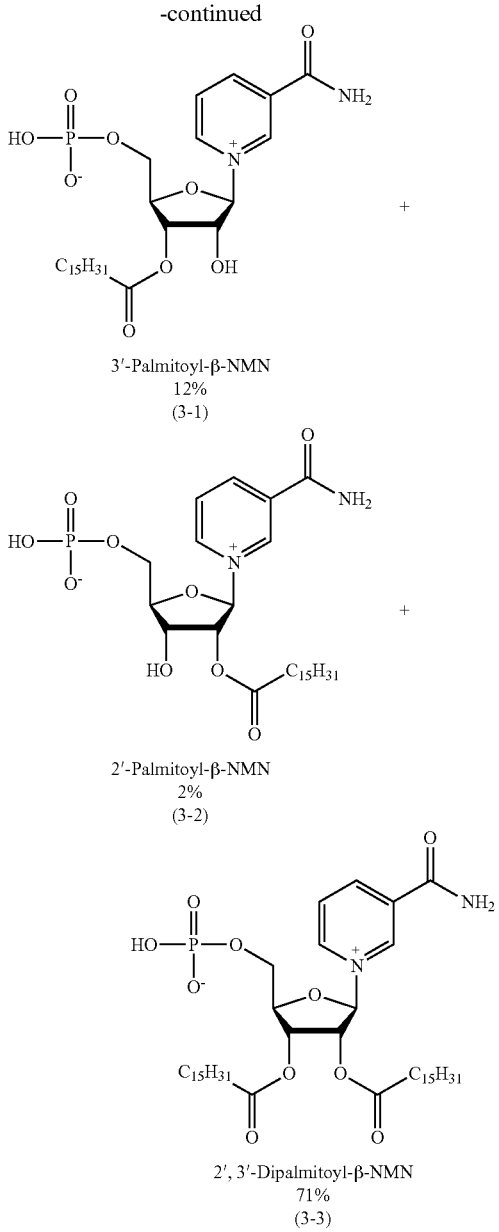

The β-nicotinamide mononucleotide (β-NMN, 0.135 g, 0.40 mmol) represented by general formula (3) above was added to trifluoroacetic acid (TFA, 5.3 mL, pKa=−0.25), which is a strongly acidic liquid, and dissolved completely followed by adding palmitoyl chloride (PaCl, 0.224 g, 0.81 mmol) as an acylating agent at room temperature (23° C.) and stirring for 1 hour. Subsequently, additional palmitoyl chloride (PaCl, 0.220 g, 0.80 mmol) was added followed by additionally stirring for 3.5 hours and acylating for a total of 4.5 hours.

Following completion of the acylation reaction, a portion of the resulting reaction liquid was sampled followed by determining the respective conversion rates and yields of the compounds represented by general formulas (3-1) to (3-3) above in the same manner as Example 1. The results are shown in Table 1.

Following completion of the acylation reaction, the reaction liquid was subjected to post-treatment in the form of concentration and drying (removal of TFA), and after adding 20 mL of hexane and washing 15 times using acetonitrile (30 mL) (confirmation of elimination of palmitic acid by quantifying under HPLC Analysis Conditions 1), the hexane layer was concentrated to obtain a white solid. The resulting white solid was then purified by combining column chromatography (silica gel and ion exchange resin) to obtain the target compound, 2',3'-dipalmitoyl-β-nicotinamide mononucleotide (2',3'-dipalmitoyl-β-NMN) represented by the aforementioned general formula (3-3), as the main component in the form of a white solid (0.151 g, isolated yield: 46%).

Table 1 shows the acylating agent used, molar ratio of acylating agent to NMN (acylating agent/NMN), solvent and isolated yield of the main component in Example 2.

The structure of the target compound was confirmed by carrying out various NMR measurements ($^1$H-NMR, $^{13}$C-NMR, $^{13}$C-DEPT135 and $^1$H-$^1$H-COSY). In addition, the target compound was confirmed to have not undergone epimerization based on the chemical shift of the proton at the 1' position of the sugar backbone and the structure of β-NMN was determined to have been retained.

The $^1$H-NMR and $^{13}$C-NMR data of the resulting 2',3'-dipalmitoyl-β-NMN are indicated below.

$^1$H-NMR (400 MHz, THF-d$_8$, 50° C.): δ (ppm)=9.61 (s, 1H), 9.38 (d, J=8.0 Hz, 1H), 9.15 (d, J=8.0 Hz, 1H), 8.42 (dd, J=8.0 and 8.0 Hz, 1H), 6.57 (d, J=4.0 Hz, 1H), 5.64 (dd, J=4.0 and 4.0 Hz, 1H), 5.54 (d, J=4.0 Hz, 1H), 4.62 (m, 1H), 4.15-4.37 (m, 2H), 2.38 (m, 4H), 1.60 (m, 4H), 1.30 (m, 48H), 0.89 (t, J=4.0 Hz, 6H)

$^{13}$C-NMR (100 MHz, THF-d$_8$, 50° C.): δ (ppm)=174.6, 166.3, 148.1, 144.4, 141.4, 136.3, 130.6, 99.3, 88.5, 77.7, 71.5, 65.6, 34.6, 33.0, 30.3-30.9, 23.7, 14.7 form), was able to be altered by adjusting the amount of palmitoyl chloride used as acylating reagent.

Examples 3, 5 and 7

Acylation reactions were carried out in the same manner as Example 1 with the exception of using the acylating agents shown in Table 1 followed by determining conversion rates and product yields in the same manner as Example 1. The results are shown in Table 1.

In addition, the reaction liquids obtained following completion of the acylation reaction were subjected to post-treatment in the same manner as Example 1, and the product after post-treatment was purified by combining column chromatography (silica gel and ion exchange resin) to obtain target compounds in the form of the main components shown in Table 1 as white solids.

Table 1 shows the acylating agent used, molar ratio of acylating agent to NMN (acylating agent/NMN), solvent and isolated yield of the main component in Examples 3, 5 and 7.

The structures of the target compounds in Examples 3, 5 and 7 were confirmed in the same manner as Example 1. The $^1$H-NMR and $^{13}$C-NMR data are indicated below.

(Example 3) 3'-lauroyl-β-NMN $^1$H-NMR (400 MHz, THF-ds/D$_2$O=5/1): δ (ppm)=9.50 (s, 1H), 9.29 (d, J=8.0 Hz, 1H), 9.03 (d, J=8.0 Hz, 1H), 8.38 (dd, J=8.0 and 8.0 Hz, 1H), 6.11 (d, J=4.0 Hz, 1H), 5.43 (d, J=4.0 Hz, 1H), 4.78 (dd, J=4.0 and 4.0 Hz, 1H), 4.59 (m, 1H), 4.04-4.32 (m, 2H), 2.44 (m, 2H), 1.61 (m, 2H), 1.27 (m, 16H), 0.85 (t, J=4.0 Hz, 3H)

TABLE 1

| | Acylating Agent | | | | | | Main |
|---|---|---|---|---|---|---|---|
| | Type | Acylating agent/NMN (molar ratio) | Solvent | Conversion Rate (%) | Yield (%) | | | Component Isolated Yield (%) |
| | | | | | 3-acylated form | 2'-acylated form | 2,3'-diacylated form | |
| Ex. 1 | PaCl | 2 | TFA | 77 | 56 | 9 | 6 | 27 |
| Ex. 2 | PaCl | 4 | TFA | 99 | 12 | 2 | 71 | 46 |
| Ex. 3 | LauCl | 2 | TFA | 79 | 58 | 10 | 6 | 30 |
| Ex. 4 | LauCl | 4 | TFA | 97 | 10 | 2 | 69 | 42 |
| Ex. 5 | OctCl | 2 | TFA | 73 | 54 | 8 | 8 | 25 |
| Ex. 6 | OctCl | 4 | TFA | 97 | 12 | 2 | 69 | 42 |
| Ex. 7 | HexCl | 2 | TFA | 74 | 54 | 7 | 8 | 35 |
| Ex. 8 | HexCl | 4 | TFA | 96 | 11 | 2 | 70 | 48 |
| Ex. 9 | PaOH | 4 | H$_2$SO$_4$ | 45 | 31 | 4 | 2 | — |
| Comp. Ex. 1 | PaCl | 6 | DMF | 98 | 0 | 0 | 0 | — |

As shown in Table 1, in Example 1, in which the amount of palmitoyl chloride used as acylating agent was 2 times the number of moles of NMN, 3'-palmitoyl-β-NMN was obtained as the main product.

In addition, in Example 2, in which the amount of palmitoyl chloride used as acylating agent was 4 times the number of moles of NMN, 2',3'-dipalmitoyl-β-NMN was obtained as the main product.

As shown in Table 1, the production ratio between a compound in which the hydroxyl group at the 3' position of the sugar backbone is acylated (3'-acylated form), a compound in which the hydroxyl group at the 2' position of the sugar backbone is acylated (2'-acylated form), and a compound in which the hydroxyl groups at the 3' position and 2' position of the sugar backbone are acylated (2',3'-diacylated $^{13}$C-NMR (100 MHz, THF-ds/D$_2$O=5/1): δ (ppm)=173.8, 165.5, 147.3, 143.6, 140.6, 135.5, 129.8, 101.2, 87.8, 77.5, 75.7, 65.4, 34.6, 32.8, 30.0-30.6, 23.6, 14.5

(Example 5) 3'-octanoyl-β-NMN $^1$H-NMR (400 MHz, THF-ds/D$_2$O=5/1): δ (ppm)=9.50 (s, 1H), 9.29 (d, J=8.0 Hz, 1H), 9.01 (d, J=8.0 Hz, 1H), 8.38 (dd, J=8.0 and 8.0 Hz, 1H), 6.11 (d, J=4.0 Hz, 1H), 5.43 (d, J=4.0 Hz, 1H), 4.78 (dd, J=4.0 and 4.0 Hz, 1H), 4.59 (m, 1H), 4.06-4.33 (m, 2H), 2.42 (m, 2H), 1.62 (m, 2H), 1.27 (m, 8H), 0.86 (t, J=4.0 Hz, 3H)

$^{13}$C-NMR (100 MHz, THF-ds/D$_2$O=5/1): δ (ppm)=173.8, 165.5, 147.3, 143.5, 140.6, 135.5, 129.8, 101.2, 87.7, 77.5, 75.7, 65.4, 34.5, 32.8, 30.2-30.6, 23.6, 14.6

(Example 7) 3'-hexanoyl-β-NMN $^1$H-NMR (400 MHz, THF-ds/D$_2$O=5/1): δ (ppm)=9.50 (s, 1H), 9.29 (d, J=8.0 Hz, 1H), 9.02 (d, J=8.0 Hz, 1H), 8.38 (dd, J=8.0 and 8.0 Hz, 1H), 6.11 (d, J=4.0 Hz, 1H), 5.43 (d, J=4.0 Hz, 1H), 4.78 (dd, J=4.0 and 4.0 Hz, 1H), 4.59 (m, 1H), 4.06-4.30 (m, 2H), 2.44 (m, 2H), 1.63 (m, 2H), 1.27 (m, 4H), 0.86 (t, J=4.0 Hz, 3H)

$^{13}$C-NMR (100 MHz, THF-ds/D$_2$O=5/1): δ (ppm)=173.8, 165.7, 147.3, 143.6, 140.6, 135.5, 129.8, 101.2, 87.7, 77.5, 75.7, 65.4, 34.6, 32.9, 30.3-30.5, 23.5, 14.6

Examples, 4, 6 and 8

Acylation reactions were carried out in the same manner as Example 2 with the exception of using the acylating agents shown in Table 1 followed by determining conversion rates and product yields in the same manner as Example 2. The results are shown in Table 1.

In addition, the reaction liquids obtained following completion of the acylation reaction were subjected to post-treatment in the same manner as Example 2, and the product after post-treatment was purified by combining column chromatography (silica gel and ion exchange resin) to obtain target compounds in the form of the main components shown in Table 1 as white solids.

Table 1 shows the acylating agent used, molar ratio of acylating agent to NMN (acylating agent/NMN), solvent and isolated yield of the main component in Examples 4, 6 and 8.

The structures of the target compounds in Examples 4, 6 and 8 were confirmed in the same manner as Example 1. The $^1$H-NMR and $^{13}$C-NMR data are indicated below.

(Example 4) 2',3'-dilauroyl-β-NMN $^1$H-NMR (400 MHz, THF-d$_8$, 50° C.): δ (ppm)=9.61 (s, 1H), 9.38 (d, J=8.0 Hz, 1H), 9.15 (d, J=8.0 Hz, 1H), 8.42 (dd, J=8.0 and 8.0 Hz, 1H), 6.57 (d, J=4.0 Hz, 1H), 5.64 (dd, J=4.0 and 4.0 Hz, 1H), 5.54 (d, J=4.0 Hz, 1H), 4.62 (m, 1H), 4.15-4.37 (m, 2H), 2.38 (m, 4H), 1.61 (m, 4H), 1.32 (m, 32H), 0.88 (t, J=4.0 Hz, 6H)

13C-NMR (100 MHz, THF-d$_8$, 50° C.): δ (ppm)=174.6, 166.3, 148.1, 144.4, 141.4, 136.3, 130.6, 99.3, 88.5, 77.7, 71.5, 65.6, 34.6, 33.0, 30.2-30.9, 23.8, 14.9

(Example 6) 2',3'-dioctanoyl-β-NMN $^1$H-NMR (400 MHz, THF-d$_8$, 50° C.): δ (ppm)=9.61 (s, 1H), 9.38 (d, J=8.0 Hz, 1H), 9.15 (d, J=8.0 Hz, 1H), 8.42 (dd, J=8.0 and 8.0 Hz, 1H), 6.57 (d, J=4.0 Hz, 1H), 5.64 (dd, J=4.0 and 4.0 Hz, 1H), 5.54 (d, J=4.0 Hz, 1H), 4.62 (m, 1H), 4.15-4.37 (m, 2H), 2.39 (m, 4H), 1.61 (m, 4H), 1.31 (m, 16H), 0.90 (t, J=4.0 Hz, 6H)

$^{13}$C-NMR (100 MHz, THF-d$_8$, 50° C.): δ (ppm)=174.6, 166.3, 148.1, 144.4, 141.4, 136.3, 130.6, 99.3, 88.5, 77.7, 71.5, 65.6, 34.6, 33.0, 30.5-30.9, 23.9, 14.8

(Example 8) 2',3'-dihexanoyl-β-NMN $^1$H-NMR (400 MHz, THF-d$_8$, 50° C.): δ (ppm)=9.61 (s, 1H), 9.38 (d, J=8.0 Hz, 1H), 9.15 (d, J=8.0 Hz, 1H), 8.42 (dd, J=8.0 and 8.0 Hz, 1H), 6.57 (d, J=4.0 Hz, 1H), 5.64 (dd, J=4.0 and 4.0 Hz, 1H), 5.54 (d, J=4.0 Hz, 1H), 4.62 (m, 1H), 4.15-4.37 (m, 2H), 2.39 (m, 4H), 1.62 (m, 4H), 1.32 (m, 8H), 0.88 (t, J=4.0 Hz, 6H)

13C-NMR (100 MHz, THF-d$_8$, 50° C.): δ (ppm)=174.6, 166.3, 148.1, 144.4, 141.4, 136.3, 130.6, 99.3, 88.5, 77.7, 71.5, 65.6, 34.6, 33.0, 30.3-30.7, 23.6, 14.6

As shown in Table 1, in the case of using a carboxylic acid chloride as the acylating agent, the 3'-acylated form of NMN was obtained as the main product (main component) in Examples 3, 5 and 7 in which the amount of acylating agent was 2 times the number of moles of NMN.

In addition, in Examples 4, 6 and 8, in which the amount of carboxylic acid chloride was 4 times the number of moles of NMN, the 2',3'-diacylated from of NMN was obtained as the main product.

As shown in Table 1, the production ratio between the 3'-acylated form, 2'-acylated form and 2',3'-diacylated form can be altered by adjusting the amount of carboxylic acid chloride used as acylating reagent.

Example 9

Synthesis of 3'-Palmitoyl-β-NMN in Sulfuric Acid Solvent

β-nicotinamide mononucleotide (β-NMN, 0.133 g, 0.40 mmol) was added to sulfuric acid (H$_2$SO$_4$, 8.0 mL, pKa was unable to be measured in water due to the acid being excessively acidic), which is a strongly acidic liquid, and completely dissolved therein followed by the addition of palmitic acid (PaOH, 0.410 g, 1.60 mmol) as an acylating agent, stirring for 12 hours and allowing to undergo acylation.

Following completion of the acylation reaction, a portion of the reaction liquid was sampled followed by quantifying the product under HPLC Analysis Conditions 1 and then quantifying the raw material under HPLC Analysis Conditions 2 to determine the conversion rate and product yield. The results are shown in Table 1.

Table 1 indicates the acylating agent used, molar ratio of acylating agent to NMN (acylating agent/NMN) and solvent in Example 9.

In addition, the structure of the product of Example 9 was confirmed by carrying out $^1$H-NMR and $^{13}$C-NMR measurements. As a result, the main component was 3'-palmitoyl-β-NMN.

As shown in Table 1, 3'-palmitoyl-β-NMN was obtained as the main product by using sulfuric acid as the strongly acidic liquid, using palmitic acid as the acylating agent, and acylating NMN at the molar ratio of acylating agent to NMN shown in Table 1.

Comparative Example 1

Palmitoylation in DMF Solvent

β-nicotinamide mononucleotide (β-NMN, 0.050 g, 0.15 mmol) was suspended in N,N-dimethylformamide (DMF, 3.0 mL) followed by the addition of pyridine (0.144 g, 1.83 mmol), immediately adding palmitoyl chloride (PaCl, 0.085 g, 0.31 mmol) at 60° C., and stirring for 3 hours. Subsequently, additional palmitoyl chloride (PaCl, 0.165 g, 0.60 mmol) was added followed by additionally stirring for 3 hours and reacting for a total of 6 hours.

Following completion of the reaction, a portion of the reaction liquid was sampled followed by quantifying the product under HPLC Analysis Conditions 1 and quantifying the raw material under HPLC Analysis Conditions 2 to determine the conversion rate and product yield. The results are shown in Table 1.

In addition, following completion of the reaction, the resulting reaction liquid was dropped into an excess amount of water, and the precipitated white solid was removed by filtration (removal of palmitic acid). The filtrate was concentrated and vacuum-dried followed by recovery of the remaining brown solid.

The structure of the product was confirmed by carrying out $^1$H-NMR and $^{13}$C-NMR measurements. As a result, the main component was nicotinic acid amide, an NMN decomposition product.

As shown in Table 1, acylated forms of NMN were not obtained in the case of using N,N-dimethylformamide as the solvent.

Synthesis Example 1

Synthesis of 2',3'-Diacetyl-β-NMN Using Acetic Anhydride

A mixed liquid of acetic anhydride (8.68 g, 85.0 mmol) as an acylating agent and pyridine (7.84 g, 99.1 mmol) was cooled to 0° C. followed by the addition thereto of an aqueous solution (0.8 mL) in which was dissolved β-nicotinamide mononucleotide (β-NMN, 0.254 g, 0.76 mmol). The mixture was stirred for 3 hours at 0° C. while monitoring the reaction by HPLC.

Following the reaction, the solvent was concentrated followed by the addition of 10 mL of water, repeating the concentration procedure and removing the residual acetic anhydride and pyridine. After dissolving the resulting residue in methanol (2.0 mL), it was dropped into ice-cold diethyl ether (40 mL), and the solid that precipitated was recovered by filtration. After again suspending and washing the recovered solid in diethyl ether, the suspension was vacuum-dried to obtain the target compound, 2',3'-diacetyl-β-nicotinamide mononucleotide (2',3'-diacetyl-β-NMN), as the main component at an isolated yield of 65%. The structure of the product was identified by $^1$H-NMR and $^{13}$C-NMR measurement.

<Skin Permeability Test>

Test substances consisting of the compounds obtained in Examples 1 to 8 and Synthesis Example 1 and β-nicotinamide mononucleotide as Comparative Example 2 were each dissolved in Dulbecco's PBS(−) solution, and after adjusting the pH of the resulting solution to 7.4 using aqueous sodium hydroxide solution and/or hydrochloric acid, the resulting solutions were used as sample solutions having a concentration of 0.2% by weight.

A three-dimensional cultured human skin model (EPI-606X, Kurabo Industries Ltd., area: 3.8 cm$^2$) was placed in a 6-well plate containing PBS solution (1 mL) so that the lower portion thereof was submerged. The human skin model was then allowed to stand undisturbed for 30 minutes in an incubator under conditions of 37° C. and a carbon dioxide concentration of 5%. Next, the PBS solution in the lower wells of the skin model was replaced with HBSS(−) solution (Hanks solution, 1 mL) (to be referred to as the "receiver liquid") and the sample solution (700 μL) obtained above was administered onto the skin model. The skin model was then allowed to stand undisturbed for 24 hours in an incubator under conditions of 37° C. and a carbon dioxide concentration of 5%.

After allowing to stand undisturbed for 24 hours, the sample solution on the skin model was removed using a pipette followed by removing the skin model from the wells and washing with PBS (−) solution. Next, a section of the skin model was cut out and placed in a 2 mL tube. Methanol (1 mL) and stainless steel beads (Tomy Co., Ltd., diameter: 5.5 mm) were added to the tube followed by crushing the section using a Multi Beads Shocker (Yasui Kikai Corp.) under conditions of 10 seconds at 2000 rpm for 10 cycles.

Following crushing, the resulting solution was transferred to a 2 mL Eppendorf tube and centrifuged for 5 minutes at 12000 rpm followed by filtering the supernatant with a filter (pore diameter: 0.22 μm) to obtain a skin model extract.

Next, the amounts of test substance in the skin model extract and receiver liquid were quantified for each test substance under the previously described HPLC Analysis Conditions 1. The total amount of test substance absorbed by the skin model in each well was calculated from the quantified value of test substance in the skin model extract. In addition, the quantified value of test substance in the receiver liquid was used as the amount of test substance that permeated the skin model. The total value A (μg) of the total amount of test substance absorbed by the skin model and the amount of test substance that permeated the skin model was then calculated.

The permeation rate (%) through the skin model for each test substance administered to the skin model was calculated according to the following equation (i). Moreover, the aforementioned skin permeability test was carried out three times for each test substance followed by calculation of each permeation rate (%). The results are shown in Table 2. In addition, Table 2 shows the main components of the compounds obtained in Examples 1 to 8 and Synthesis Example 1. Furthermore, the value shown in front of the (±) symbol in the column entitled "Permeation Rate (%)" indicates the average value of the three results, while the number after the (±) symbol indicates the range of variation of the three results.

Permeation rate (%)=($A$/1400(amount of test substance administered to skin model) (μg)))×100    (i)

TABLE 2

| | Test Compound (Main Component) | Permeation Rate (%) |
|---|---|---|
| Example 1 | 3'-palmitoyl-β-NMN | 40 ± 4.7 |
| Example 2 | 2',3'-dipalmitoyl-β-NMN | 41 ± 1.7 |
| Example 3 | 3'-lauroyl-β-NMN | 35 ± 4.7 |
| Example 4 | 2',3'-dilauroyl-β-NMN | 40 ± 4.7 |
| Example 5 | 3'-octanoyl-β-NMN | 31 ± 4.7 |
| Example 6 | 2',3'-dioctanoyl-β-NMN | 38 ± 4.7 |
| Example 7 | 3'-hexanoyl-β-NMN | 29 ± 4.7 |
| Example 8 | 2',3'-dihexanoyl-β-NMN | 37 ± 2.7 |
| Synthesis Example 1 | 2',3'-diacetyl-β-NMN | 16 ± 1.7 |
| Comparative Example 2 | β-NMN | 15 ± 0.4 |
| Example 11 | 2',3'-dipalmitoyl-β-NMN sodium salt | 41 ± 2.7 |

As shown in Table 2, the compounds obtained in Examples 1 to 8 in the form of acylated β-NMN derivatives demonstrated higher permeation rates in comparison with the non-acylated β-NMN of Comparative Example 2.

Among Examples 1 to 8, permeation rates were particularly high for Examples 1 and 2 (number of carbon atoms: 16) and Examples 3 and 4 (number of carbon atoms: 12), which have a large number of carbon atoms in the acyl group on the sugar backbone of NMN.

In contrast, since the compound obtained in Synthesis Example 1 in the form of an acylated β-NMN derivative has a small number of carbons (number of carbon atoms: 2) in the acyl groups at the 3' position and 2' position of the sugar backbone of NMN, the permeation rate thereof is equal to that of the non-acylated β-NMN of Comparative Example 2.

In this manner, compounds according to the present invention demonstrated remarkably high permeation rates among β-NMN derivatives, and were indicated to be extremely superior as active ingredients of topical skin preparations.

<Water Solubility Test>

Test substances consisting of the compounds obtained in Examples 1 to 8 and Synthesis Example 1 and 3-nicotinamide mononucleotide as Comparative Example 2 were each tested for solubility in water according to the procedure indicated below.

1 g, 0.1 g and 0.01 g aliquots of each test substance were weighed out in 100 mL glass vials. 100 mL of purified water was added thereto followed by stirring well, allowing to stand undisturbed, and visually assessing the state of the solution 16 hours later according to the criteria indicated below. The results are shown in Table 3. In addition, the main components of the compounds obtained in Examples 1 to 8 and Synthesis Example 1 are shown in Table 3.

[Criteria]
A: Clear
B: Turbid with no precipitation
C: Turbid with precipitation

TABLE 3

| | | Water Solubility | | |
|---|---|---|---|---|
| | Test Compound (Main Component) | 1 g/100 mL | 0.1 g/100 mL | 0.01 g/100 mL |
| Example 1 | 3'-palmitoyl-β-NMN | C | A | A |
| Example 2 | 2',3'-dipalmitoyl-β-NMN | C | B | A |
| Example 3 | 3'-lauroyl-β-NMN | A | A | A |
| Example 4 | 2',3'-dilauroyl-β-NMN | A | A | A |
| Example 5 | 3'-octanoyl-β-NMN | A | A | A |
| Example 6 | 2',3'-dioctanoyl-β-NMN | A | A | A |
| Example 7 | 3'-hexanoyl-β-NMN | A | A | A |
| Example 8 | 2',3'-dihexanoyl-β-NMN | A | A | A |
| Synthesis Example 1 | 2',3'-diacetyl-β-NMN | A | A | A |
| Comparative Example 2 | β-NMN | A | A | A |
| Example 11 | 2',3'-dipalmitoyl-β-NMN sodium salt | C | B | A |

As shown in Table 3, the compounds of Examples 1 to 8 in the form of acylated β-NMN derivatives were all evaluated as "A" in the case of evaluating at 0.01 g/100 mL, and were confirmed to have adequate water solubility.

Among Examples 1 to 8, Examples 3 and 4 (number of carbon atoms: 12), Examples 5 and 6 (number of carbon atoms: 8) and Examples 7 and 8 (number of carbon atoms: 6), which have a small number of carbon atoms in the acyl group on the sugar backbone of NMN, were all evaluated as "A" at 1 g/100 mL, 0.1 g/100 mL and 0.01 g/100 mL, and demonstrated high water solubility.

Example 10

Preparation of 2',3'-Dipalmitoyl-β-NMN Hydrochloride

The 2',3'-dipalmitoyl-β-nicotinamide mononucleotide produced in Example 2 was subjected to reduced pressure treatment to adequately remove any moisture. After removing the moisture, 3 mL of hydrogen chloride (4 mol/L, 1,4-dioxane solution, Tokyo Chemical Industry Co., Ltd.) were added under nitrogen atmosphere to dissolve 2',3'-dipalmitoyl-β-nicotinamide mononucleotide (0.050 g, 0.062 mmol), followed by stirring for 10 minutes. After stirring, the solution was concentrated under reduced pressure to distill off excess hydrogen chloride (4 mol/L, 1,4-dioxane solution). Following distillation, the residue was vacuum-dried to obtain the target compound, 2',3'-dipalmitoyl-β-NMN hydrochloride, as a white solid (0.052 g, 0.062 mmol).

The chloride ion concentration in the resulting 2',3'-dipalmitoyl-β-NMN hydrochloride was quantified by ion chromatography under the conditions indicated below. As a result, the NMN derivative functioning as a cation and the anion ($Cl^-$) derived from the hydrogen chloride were confirmed to have formed a salt at a molar ratio of nearly 1:1.

(Ion Chromatography Analysis Conditions)
Column: Dionex Ion Pack AS12A (trade name, Dionex Corp.)
Eluent: 2.7 mM aqueous sodium carbonate solution/0.3 mM aqueous sodium bicarbonate solution
Flow rate: 1.2 mL/min
Column temperature: 40° C.
Detector: Conductivity meter Example 11

Preparation of 2',3'-Dipalmitoyl-β-NMN Sodium Salt

The 2',3'-dipalmitoyl-β-nicotinamide mononucleotide produced in Example 2 was subjected to reduced pressure treatment to adequately remove any moisture. After removing the moisture, 3 mL of methanol were added to the 2',3'-dipalmitoyl-3-nicotinamide mononucleotide (0.050 g, 0.062 mmol) followed by the addition of 0.01 mol/L aqueous sodium hydroxide solution (0.062 mmol, 6.2 mL, Junsei Chemical Co., Ltd.) while stirring at room temperature, followed by stirring for 10 minutes. Subsequently, the solution was concentrated and dried at room temperature to obtain the target compound, 2',3'-dipalmitoyl-β-NMN sodium salt, as a white solid (0.052 g, 0.062 mmol).

The sodium ion concentration in the resulting 2',3'-dipalmitoyl-β-NMN sodium salt was quantified by ion chromatography under the conditions indicated below. As a result, the NMN derivative functioning as an anion and the cation ($Na^+$) derived from the sodium hydroxide were confirmed to have formed a salt at a molar ratio of nearly 1:1.

(Ion Chromatography Analysis Conditions)
Column: Dionex Ion Pack CS12A (trade name, Dionex Corp.)
Eluent: 20 mM aqueous methanesulfonate solution
Flow rate: 1.0 mL/min
Column temperature: 40° C.
Detector: Conductivity meter A skin permeability test and water solubility test were carried out in the same manner as Example 1 using the 2',3'-dipalmitoyl-β-NMN sodium salt obtained in Example 11 as the test substance. The results of the skin permeability test are shown in Table 2. In addition, the results of the water solubility test are shown in Table 3.

As shown in Table 2, the compound obtained in Example 11 (salt of acylated β-NMN derivative) demonstrated a high permeation rate in comparison with the non-acylated β-NMN of Comparative Example 2. In addition, as shown in Table 3, the compound obtained in Example 11 was evaluated as "A" in the case of 0.01 g/100 mL and was confirmed to have adequate water solubility.

The invention claimed is:

1. A nicotinamide mononucleotide derivative, or salt thereof, which is a compound represented by general formula (1):

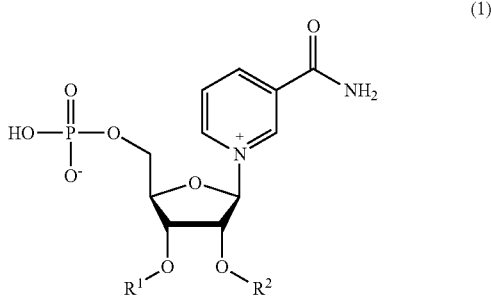

wherein, $R^1$ and $R^2$ respectively and independently represent a hydrogen atom or an acyl group having 3 to 30 carbon atoms, wherein the hydrocarbon group bound to the carbonyl carbon of the acyl group is a linear or branched, saturated or unsaturated hydrocarbon group, and at least one of $R^1$ and $R^2$ is an acyl group.

2. The nicotinamide mononucleotide derivative, or salt thereof, according to claim 1, wherein $R^1$ and $R^2$ in the general formula (1) respectively and independently represent an acyl group having 6 to 16 carbon atoms.

3. The nicotinamide mononucleotide derivative, or salt thereof, according to claim 1, wherein the salt of the compound of the general formula (1) is a salt formed with one or more types of anions selected from the group consisting of: nitrate ions, sulfate ions, carbonate ions, bicarbonate ions, halide ions, formate ions, acetate ions, citrate ions, tartrate ions, oxalate ions, fumarate ions, anions of saturated or unsaturated fatty acids having 3 to 20 carbon atoms, anions of carnitine, anions of hydroxycitric acid, anions of ascorbic acid, and anions of ascorbyl phosphate.

4. The nicotinamide mononucleotide derivative, or salt thereof, according to claim 1, wherein the salt of the compound of the general formula (1) is a salt formed with one or more types of cations selected from the group consisting of: sodium ions, potassium ions, calcium ions, magnesium ions, zinc ions, ammonium ions, and cations of carnitine.

5. A method for producing the nicotinamide mononucleotide derivative, or salt thereof, according to claim 1, comprising: acylating nicotinamide mononucleotide with one or more types of acylating agents selected from the group consisting of: carboxylic acids having an acyl group having 3 to 30 carbon atoms, in which a linear or branched, saturated or unsaturated hydrocarbon group is bound to the carbonyl carbon; a halide of the carboxylic acid, and an anhydride of the carboxylic acid, in a solvent containing 20% by weight or more of a strongly acidic liquid having $pK_a$ of 2.0 or less.

6. The method for producing the nicotinamide mononucleotide derivative, or salt thereof, according to claim 5, wherein the strongly acidic liquid is trifluoroacetic acid or sulfuric acid.

7. A nicotinamide mononucleotide derivative-containing or nicotinamide mononucleotide derivative salt-containing topical skin composition comprising the nicotinamide mononucleotide derivative, or a salt thereof, according to claim 1, and optionally one or more additional ingredients suitable for the topical skin composition.

8. A nicotinamide mononucleotide derivative-containing or nicotinamide mononucleotide derivative salt-containing cosmetic comprising the topical skin composition according to claim 7, and optionally one or more additional ingredients suitable for the cosmetic.

9. A nicotinamide mononucleotide derivative-containing or nicotinamide mononucleotide derivative salt-containing food additive comprising the nicotinamide mononucleotide derivative, or a salt thereof, according to claim 1, and optionally one or more additional ingredients suitable for the food additive.

* * * * *